United States Patent [19]

Barr

[11] 4,329,333

[45] May 11, 1982

[54] METHOD FOR THE ORAL TREATMENT OF DOGS AND OTHER ANIMALS

[76] Inventor: Arthur Barr, 2942 Shore Dr., Merrick, N.Y. 11566

[21] Appl. No.: 209,933

[22] Filed: Nov. 24, 1980

[51] Int. Cl.$^3$ .......................... A61K 9/50; A61K 9/06; A61L 15/03; A61F 13/00

[52] U.S. Cl. ....................................... 424/19; 424/20; 424/22; 424/28; 424/49; 424/51; 424/54; 424/78; 128/268

[58] Field of Search ................................. 424/19–22, 424/28, 49–58; 128/268

[56] References Cited

U.S. PATENT DOCUMENTS

| | | | |
|---|---|---|---|
| 3,029,187 | 4/1962 | Steinhardt et al. | 424/52 |
| 3,249,109 | 5/1966 | Maeth | 128/268 |
| 3,312,594 | 4/1967 | Cyr et al. | 424/361 |
| 3,339,546 | 9/1967 | Chen | 128/268 |
| 3,598,123 | 8/1971 | Zaffaroni | 128/268 |
| 3,731,683 | 5/1973 | Zaffaroni | 128/268 |
| 3,911,099 | 10/1975 | DeFoney et al. | 424/28 |
| 3,957,964 | 5/1976 | Grimm | 424/10 |
| 3,971,852 | 7/1976 | Brenner et al. | 426/103 |
| 3,972,995 | 8/1976 | Tsuk et al. | 424/28 |
| 4,059,686 | 11/1977 | Tanaka et al. | 424/19 |
| 4,250,163 | 2/1981 | Nagai et al. | 424/14 |

*Primary Examiner*—Shep K. Rose
*Attorney, Agent, or Firm*—Hane, Roberts, Spiecens & Cohen

[57] ABSTRACT

Method for oral treatment of dogs and other animals comprising administering a composition having slow release to the gums of dogs, the composition comprising a multiplicity of microencapsulated liquid droplets of flavoring material and anti-plaque agents contained in a carrier. The microencapsulated droplets are soluble in the saliva in the mouth to release the flavoring material and anti-plaque agents. The flavoring material is released at a sustained rate for long periods of time in the mouth to mask mouth odor while the anti-plaque agent prevents plaque build-up during release and in the case of chlorohexidine acetate for several hours thereafter.

13 Claims, No Drawings

४,३२९,३३३

METHOD FOR THE ORAL TREATMENT OF DOGS AND OTHER ANIMALS

FIELD OF THE INVENTION

The invention relates to the oral treatment of dogs and other animals and particularly the use of compositions capable of slow release, at a sustained rate, of microencapsulated agents. The agents may comprise liquid flavoring materials to eliminate bad breath, an anti-plaque agent, and a deworming agent.

BACKGROUND

Dogs and other animals generally develop bad mouth odor from a number of causes including plaque formation on their teeth especially as the dog ages.

Up to the present, no satisfactory compositions or methods have been produced which will overcome bad mouth odor in dogs or other animals for long periods of time, and despite the wide-spread use of various charcoal flavored food products and sprays, there has been no effective long-term solution to overcome the problem of offensive mouth odor.

In order to eliminate offensive mouth odor in dogs and other animals, it is necessary to anesthetize the animal and remove plaque formation by mechanical means. This is not only expensive but uncomfortable for the dog.

SUMMARY OF THE INVENTION

An object of the invention is to provide a method for topical application to the gums or teeth of dogs of a composition having slow release in the mouth and capable of eliminating offensive breath and opposing the formation of plaque, a major cause of bad breath.

A further object of the invention is to provide a composition as above which will be effective to treat worms and other animal parasites.

According to a feature of the invention, the composition may be in the form of a paste, cream, or gel adapted for application directly to the gums or teeth of the animal.

In accordance with the invention, there is provided a composition having slow release adapted for topical application to the gums of dogs and other animals comprising a multiplicity of microencapsulated liquid droplets of flavoring materials, an anti-plaque agent and optionally an anti-parasitic agent, the microencapsulated droplets being soluble in the saliva of the mouth to slowly release the microencapsulated materials when entering into contact with the saliva. As a consequence, the microencapsulates can slowly release the liquid materials at a sustained rate. The microencapsulates are present in a base which has adhesive properties and therefore will adhere to the gums of the animal. In a modified form, the base is constituted as a membraneous wafer having an adhesive incorporated therein.

In accordance with a specific embodiment of the invention, the encapsulated materials are present in an amount of 3–15% by weight of the composition. The base is present as a remainder of 85–97% and comprises petrolatum and karaya gum. The gum can be present in an amount of 51% by weight of the composition and the petrolatum in an amount of 30% by weight of the composition.

DESCRIPTION OF PREFERRED EMBODIMENTS

In order to confer a slow sustained release of flavoring materials into the mouth of a dog or other animal to mask breath odor there is employed a multiplicity of microencapsulated liquid droplets of flavoring materials in a prepared base composition. The encapsulated droplets are soluble in the saliva in the mouth of the animal so as to dissolve the microencapsulation material and release the flavoring material when entering into contact with saliva in the mouth.

The formation of microencapsulated liquid droplets of material is well known in the art and does not form any part of the present invention. Hence, it will not be described at length herein. However, for the purpose of brief explanation, reference is made to the publication "Microencapsulation" by Herbig as presented in the "Encyclopedia of Chemical Technology" of Kirk-Othmer, Volume 13, 2nd Edition, pp 436–456. As disclosed herein, minute particles or liquid droplets of material can be encased by an impervious capsule wall and isolated from the surrounding atmosphere.

In the circumstances of the present invention, flavoring material and an anti-plaque agent are encapsulated in liquid form in a non-water soluble coating and the coating may be of varying wall thickness in order to provide for sustained release of the liquid material over a period of time, of the order of several hours, when the encapsulated droplets come into contact with saliva in the mouth of the animal. The encapsulating material must satisfy the purposes of the invention of being saliva-soluble and providing sustained release of the encapsulated material while being not soluble in water and thus capable of long shelf life without weight loss to the ambient atmosphere. Furthermore, because of this property, breakdown of capsules will not be speeded up by intake of drinking water or other watercontaining beverages by the animal.

The multiplicity of microencapsulated liquid droplets is incorporated into a base and the base may take one of many different forms. In one form, the base is consituted as a paste, cream or gel which can be placed on the gums of the animal to slowly release the encapsulated materials over a period of time. In a modification, the anti-plaque agent can be separately encapsulated or directly contained by admixture in the paste, cream or gel. In a further modification, the base incorporating the microencapsulates of liquid droplets can be formed as a membraneous wafer having an adhesive incorporated therein whereby the wafer can be affixed to the palate or gums of the animal to slowly release the encapsulated materials. The wafer can be thus utilized to provide protection against mouth odor for several hours. The length of protection is based upon the amount of product used.

The flavoring materials can be of wide range and by way of example, it may be mint flavor such as spearmint, peppermint, oil of wintergreen, etc. Also, useable are fruit flavors or other flavorings such as vanillin and menthol.

The anti-plaque agent can be any known agent suitable for preventing plaque build-up in dogs including, for example, chlorohexidine acetate, benzethonium chloride, povidone iodine, etc.

Chlorohexidine acetate is especially effective as an anti-plaque agent in microencapsulated form since it not only acts continuously for several hours during the slow release but it continues to act for several hours after disintegration of the capsules. In this regard, chlorohexidine acetate is retained at anti-bacterial levels within the oral cavity after complete dissolution of the microencapsulate material.

The flavoring materials and anti-plaque agents are present in substantially equal amounts and collectively they represent 3-15% by weight of the composition.

The base which represents the remainder of the composition is present in an amount of 85-97% by weight and serves as the vehicle for containing the encapsulated material distributed therethroughout.

The base or carrier for the encapsulated material is in the form of a mixture of a gum in a petrolatum base. Specifically, a gum such as karaya gum in an amount of 51% is mixed with 30% by weight of petrolatum. Additionally, contained in the carrier is mineral oil in an amount of about 12%. If it is desired to make the composition of a softer consistency, the petrolatum is reduced in an amount of the order of 1-2% and the amount of mineral oil is increased by this same amount.

The carrier can contain additional substances and these include a small percentage of titanium dioxide as a whitener and a small percentage of propylparaben as an antifungicide.

Additionally, the carrier can contain an anthelmintic agent such as piperazine adipate to make the composition effective against worms and other parasites. The amount of the anthelmintic agent is generally a function of the weight of the dog and daily amounts between 100 and 500 mg are indicated. The anthelmintic agent should be present in an amount of between 5 and 15% weight of the composition. The anthelmintic agent may also be encapsulated to provide sustained release and long lasting effectiveness, particularly in the case of smaller animals since most anthelmintic agents have the unwanted effect of creating diarrhea and vomiting if given in larger doses.

As a further feature of the invention, the long lasting flavor in the animal's mouth tends to diminish its appetite. The product therefore can be used to control the wight of animals i.e. overweight dogs, show dogs and cats, and dogs that chew household items because they are hungry between meals.

EXAMPLES

Microencapsulated droplets were prepared by encapsulating peppermint flavoring, and chlorhexidine acetate in liquid droplet form in an encapsulating material which is substantially not soluble in water but is soluble in saliva in the mouth of the user.

A microencapsulated droplet composition prepared according to the invention includes the following components in % by weight:

| | |
|---|---|
| liquid peppermint | 46% |
| chlorhexidine acetate | 45% |
| gelatin | 4.25% |
| gum arabic | 4.25% |
| glutaraldehyde (gelatin cross-linking agent) | .25% |
| sodium silicate (Aerosil 972) | .25% |

The microencapsulated droplets have a size of between 10 and 400 microns and a wall thickness of less than 5 microns and generally between 2 and 3 microns. The droplets were found to have a maximum weight loss in air of about 10% which was achieved within about 9 days whereafter there was no further weight loss. The microencapsulated droplets were not soluble in water but were slowly soluble in saliva in the mouth of the user.

The following composition of the invention was prepared by the method to be described hereafter.

| INGREDIENT | PERCENT BY WEIGHT |
|---|---|
| Microencapsulated droplets (as prepared above) | 6 |
| Karaya gum | 51 |
| Petrolatum | 30 |
| Mineral oil | 12.4 |
| Titanium dioxide | 0.5 |
| Propylparaben | 0.1 |

The composition was prepared by first premilling the titanium dioxide in 4.5% by weight of the mineral oil to prepare a 10% dispersion.

The remainder or 7.9% of the mineral oil was added to a jacketed stainless steel kettle equipped with side scraping sweep agitation. To the kettle was then added the propylparaben the petrolatum and the titanium dioxide dispersion. The mixture was heated to a temperature of 55° with agitation.

The karaya gum was then added and mixing was continued until a uniform mixture was obtained. The encapsulated material was then added and mixing was continued until the encapsulated material was uniformly distributed throughout the mixture.

The mixture was then transferred at a temperature of 50° C. to a filling station where tubes were filled with the mixture.

In use, the composition was applied to the upper gums adjacent the cheeks of dogs and for this purpose one or two small dabs was found to be sufficient. The flavoring and anti-plaque material was found to be slowly released in situ in the mouth at a sustained rate. It was found that the composition is effective for long periods of time of the order of 4-8 hours.

Although the invention has been described in conjunction with a specific embodiment thereof it will be apparent to those skilled in the art that numerous modifications and variations can be undertaken without departing from the scope and spirit of the invention as defined in the attached claims.

What is claimed is:

1. A method for the oral treatment of dogs, said method comprising forming a paste composition consisting essentially of microencapsulated droplets of liquid flavoring material and an anti-plaque agent in a paste carrier, said microencapsulated droplets being constituted of a coating which is substantially non-soluble in water but is soluble in the saliva of the mouth of a dog, said paste carrier being adhesive, adhering a quantity of the composition in the oral cavity of the dog whereafter the flavoring material and anti-plaque agent are conjointly slowly released in situ in the mouth at a sustained rate, the composition of the liquid flavoring material and anti-plaque agent and their encapsulation in the carrier being such that the droplets of material are slowly dissolved and mask mouth odor of the animal while the anti-plaque agent acts to inhibit plaque formation.

2. A method as claimed in claim 1 wherein the microencapsulated material is present in an amount of 3-15% by weight of the paste composition.

3. A method as claimed in claims 1 or 2 wherein said flavoring material and anti-plaque agent are present in substantially equal amounts in said paste composition.

4. A method as claimed in claim 3 wherein said anti-plaque agent is microencapsulated with said flavoring material.

5. A method as claimed in claim 2 wherein the flavoring material is a mint flavored material.

6. A method as claimed in claim 1 wherein said paste carrier is present in an amount of 85–97% by weight and comprises petrolatum and gum.

7. A method as claimed in claim 4 wherein the gum is karaya gum.

8. A method as claimed in claim 4 wherein the paste carrier further comprises mineral oil.

9. A method as claimed in claim 6 wherein the paste carrier further comprises titanium dioxide as a colorant.

10. A method as claimed in claim 1 wherein said microencapsulated droplets consist essentially of the following in percent by weight:

| | |
|---|---|
| Liquid flavoring material | 46% |
| Anti-plaque agent | 45% |
| Gelatin | 4.25% |
| Gum arabic | 4.25% |
| Glutaraldehyde | .25% |
| Sodium silicate | .25%. |

11. A method as claimed in claim 10 wherein the microencapsulated droplets are present in an amount of 6% by weight and the paste carrier consists of the following by weight:

| | |
|---|---|
| Karaya gum | 51% |
| Petrolatum | 30% |
| Propylparaben | 0.1% |
| Mineral Oil | 12.4% |
| Titanium dioxide | 0.4%. |

12. A method as claimed in claim 1 comprising incorporating a therapeutically active amount of anthelmintic agent in said carrier.

13. A method as claimed in claim 12 comprising providing said anthelmintic agent in encapsulated form.

* * * * *